United States Patent
Isshiki

(10) Patent No.: US 8,632,169 B2
(45) Date of Patent: Jan. 21, 2014

(54) LIQUID EJECTING HEAD, LIQUID EJECTING APPARATUS, PIEZOELECTRIC ELEMENT, AND METHOD FOR EVALUATING PIEZOELECTRIC LAYER

(71) Applicant: Seiko Epson Corporation, Tokyo (JP)

(72) Inventor: Tetsuya Isshiki, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 13/763,766

(22) Filed: Feb. 11, 2013

(65) Prior Publication Data

US 2013/0208054 A1  Aug. 15, 2013

(30) Foreign Application Priority Data

Feb. 13, 2012 (JP) ................................. 2012-028964

(51) Int. Cl.
- *B41J 2/045* (2006.01)
- *C04B 35/495* (2006.01)
- *H01L 41/18* (2006.01)
- *H01L 41/187* (2006.01)
- *C04B 35/00* (2006.01)

(52) U.S. Cl.
USPC .................. 347/68; 252/62.9 R; 252/62.9 PZ

(58) Field of Classification Search
USPC ............ 347/68; 310/65; 252/62.9 R, 62.9 PZ
See application file for complete search history.

(56) References Cited

U.S. PATENT DOCUMENTS 7,019,438 B2 * 3/2006 Takahashi et al. ............ 310/324
2007/0241642 A1   10/2007 Miyazawa et al.

FOREIGN PATENT DOCUMENTS

| JP | 2001-019543 | 1/2001 |
| JP | 2001-223404 | 8/2001 |
| JP | 2007-287745 | 11/2007 |
| JP | 2011029481 A * | 2/2011 |

* cited by examiner

*Primary Examiner* — Lisa M Solomon
(74) *Attorney, Agent, or Firm* — Harness, Dickey & Pierce, P.L.C.

(57) ABSTRACT

A liquid ejecting head includes a piezoelectric element including a piezoelectric layer made of a piezoelectric material and an electrode disposed on the piezoelectric layer. The piezoelectric material is such that when a diamond conical indenter having an angle α of 136° between opposite faces is pressed into the piezoelectric layer at a load of 5 gf for 5 seconds to form cracks extending from an indentation, using a micro Vickers hardness meter, the length of the cracks from four corners of the indentation is 15 μm or less.

6 Claims, 8 Drawing Sheets

LIQUID EJECTING HEAD, LIQUID EJECTING APPARATUS, PIEZOELECTRIC ELEMENT, AND METHOD FOR EVALUATING PIEZOELECTRIC LAYER

The entire disclosure of Japanese Patent Application No. 2012-028964, filed Feb. 13, 2012 is expressly incorporated by reference herein.

BACKGROUND

1. Technical Field

The present invention relates to a piezoelectric element including a piezoelectric layer made of a piezoelectric material and electrodes, and to a liquid ejecting head and a liquid ejecting apparatus that each include the piezoelectric element and that eject droplets from nozzle apertures. The invention also relates to a method for evaluating the piezoelectric layer.

2. Related Art

Ink jet recording heads are a typical type of liquid ejecting head. For example, an ink jet recording head includes a vibration plate defining a part of a pressure generating chamber communicating with nozzles through which ink droplets are discharged. In the ink jet recording head, a piezoelectric element deforms a vibration plate to apply a pressure to the ink in the pressure generating chamber, thereby discharging ink droplets through the nozzles. Some of the piezoelectric elements used in ink jet recording heads have a structure in which a piezoelectric layer (piezoelectric film) made of a piezoelectric material capable of electromechanical conversion, such as a crystallized dielectric material, is disposed between two electrodes.

The piezoelectric material used for forming the piezoelectric layer of such a piezoelectric element is required to have high piezoelectric properties, and a typical example of the piezoelectric material is lead zirconate titanate (PZT) (see JP-A-2001-223404 and JP-A-2001-19543). In addition, in view of environmental issues, it is desirable that the piezoelectric material contain no lead or a reduced amount of lead. For example, JPA-2007-287745 discloses a lead-free piezoelectric material containing Bi, Ba, Fe and Ti.

Although various types of piezoelectric material are used for the piezoelectric layer, cracks can occur in the piezoelectric layer of any type of piezoelectric material. This problem can arise not only in liquid ejecting heads, a representative example of which is an ink jet recording head, but also in piezoelectric elements used for other applications.

SUMMARY

Accordingly, an advantage of some aspects of the invention is that it provides a piezoelectric element including a piezoelectric layer in which the occurrence of cracks is suppressed, and also provides a liquid ejecting head and a liquid ejecting apparatus that each include the piezoelectric element, and a method for evaluating the piezoelectric layer.

According to an aspect of the invention, a liquid ejecting head that ejects a liquid through a nozzle aperture is provided. The liquid ejecting head includes a piezoelectric element including a piezoelectric layer made of a piezoelectric material and an electrode disposed on the piezoelectric layer. The piezoelectric material is such that when a diamond conical indenter having an angle of 136° between opposite faces is pressed into the piezoelectric layer at a load of 5 gf for 5 seconds to form cracks extending from an indentation, using a micro Vickers hardness meter, the length of the cracks from four corners of the indentation is 15 μm or less.

By forming the piezoelectric layer of such a piezoelectric material, the occurrence of cracks in the piezoelectric layer can be suppressed.

The piezoelectric material may be a complex oxide having a perovskite structure and containing bismuth, iron, barium and titanium. In the piezoelectric layer made of such a piezoelectric material, the occurrence of cracks can be suppressed. In addition, since the piezoelectric material contains little or no lead, the environmental load of the liquid ejecting head is reduced.

According to another aspect of the invention, a liquid ejection apparatus including the above-described liquid ejecting head is provided. Since the liquid ejecting head includes a piezoelectric layer in which the occurrence of cracks is suppressed, the liquid ejecting apparatus is highly reliable.

According to still another aspect of the invention, a piezoelectric element is provided which includes a piezoelectric layer made of a piezoelectric material and an electrode disposed on the piezoelectric layer. The piezoelectric material is such that when a diamond conical indenter having an angle of 136° between opposite faces is pressed into the piezoelectric layer at a load of 5 gf for 5 seconds to form cracks extending from an indentation, using a micro Vickers hardness meter, the length of the cracks from four corners of the indentation is 15 μm or less. By forming the piezoelectric layer of such a piezoelectric material, the occurrence of cracks in the piezoelectric layer can be suppressed.

According to still another aspect of the invention, a method for evaluating a piezoelectric layer is provided. The method includes pressing a diamond conical indenter having an angle of 136° between opposite faces into the piezoelectric layer at a load of 5 gf for 5 seconds using a micro Vickers hardness meter, thereby forming cracks extending from an indentation, and measuring the length of the cracks from four corners of the indentation. The length of the cracks extending from the four corners of the indentation formed by this method has a high correlation with the occurrence of cracks in the piezoelectric layer. Therefore, by measuring this length of the cracks, how easily the piezoelectric layer cracks can be evaluated.

BRIEF DESCRIPTION OF THE DRAWINGS

The invention will be described with reference to the accompanying drawings, wherein like numbers reference like elements.

DESCRIPTION OF EXEMPLARY EMBODIMENTS

Exemplary Embodiment

Figure 1:
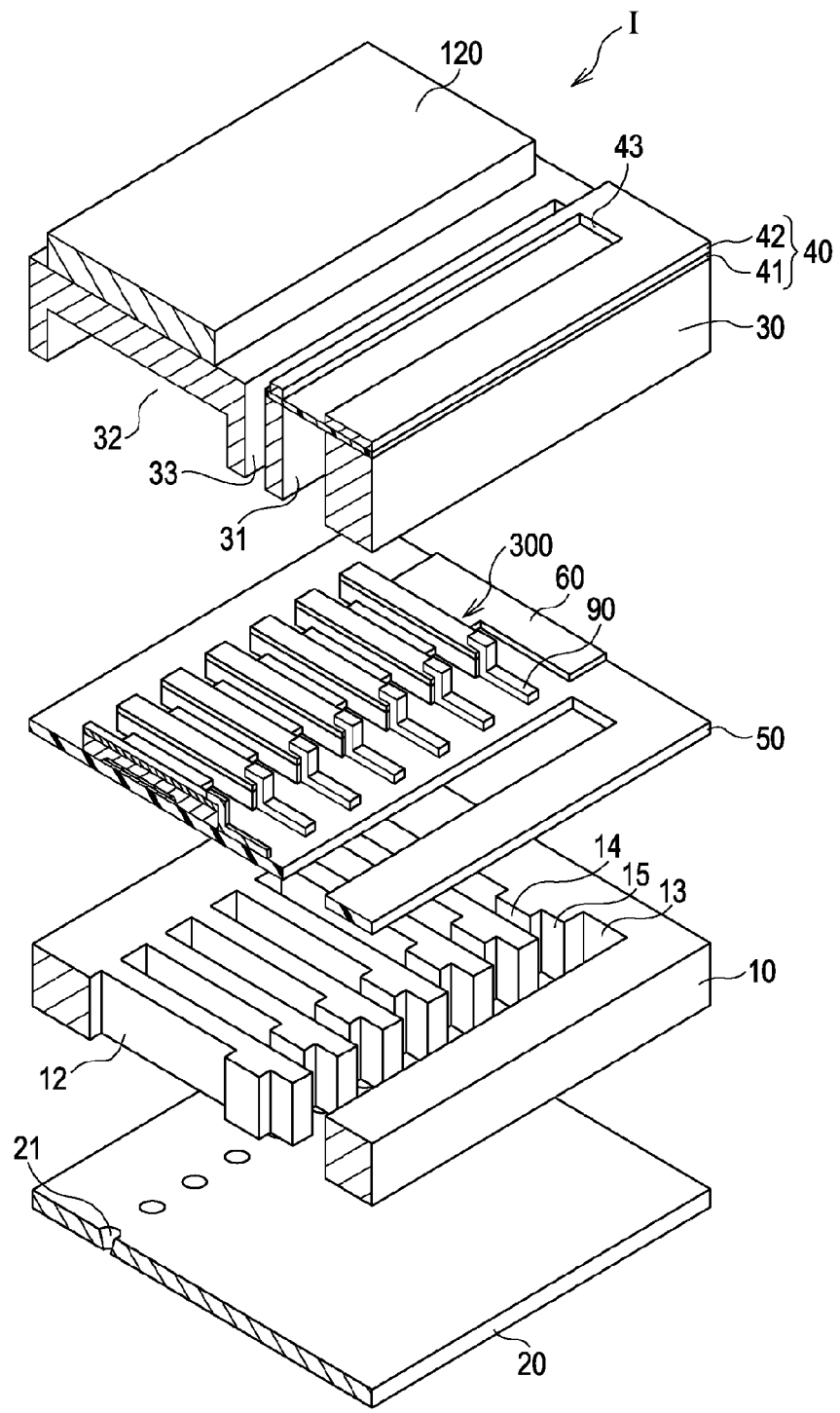
FIG. 1 is a schematic exploded perspective view of a recording head according to an embodiment of the invention.
Figure 2:
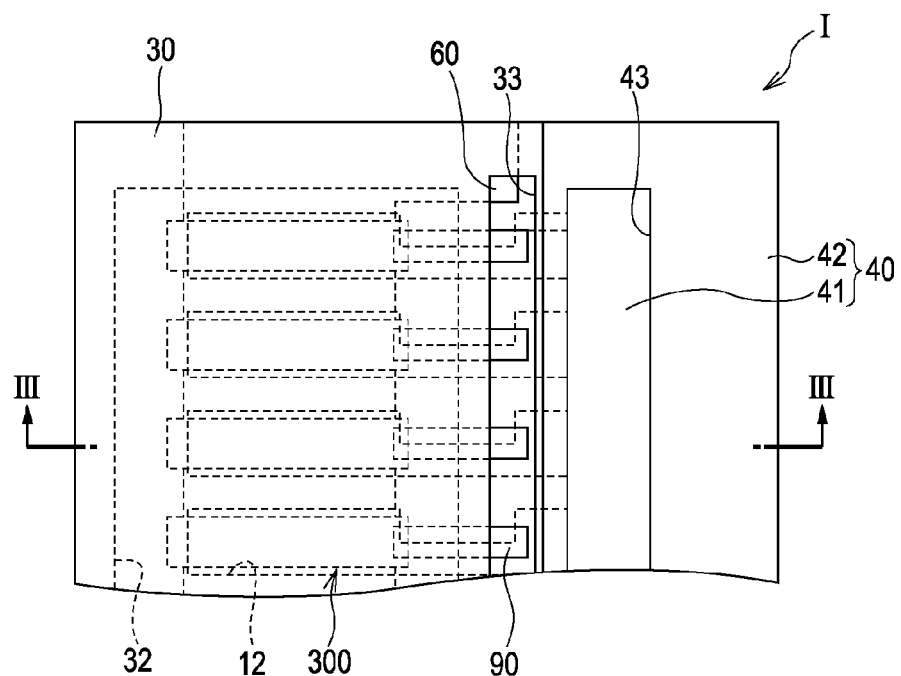
FIG. 2 is a plan view of the recording head according to the embodiment.
Figure 3:
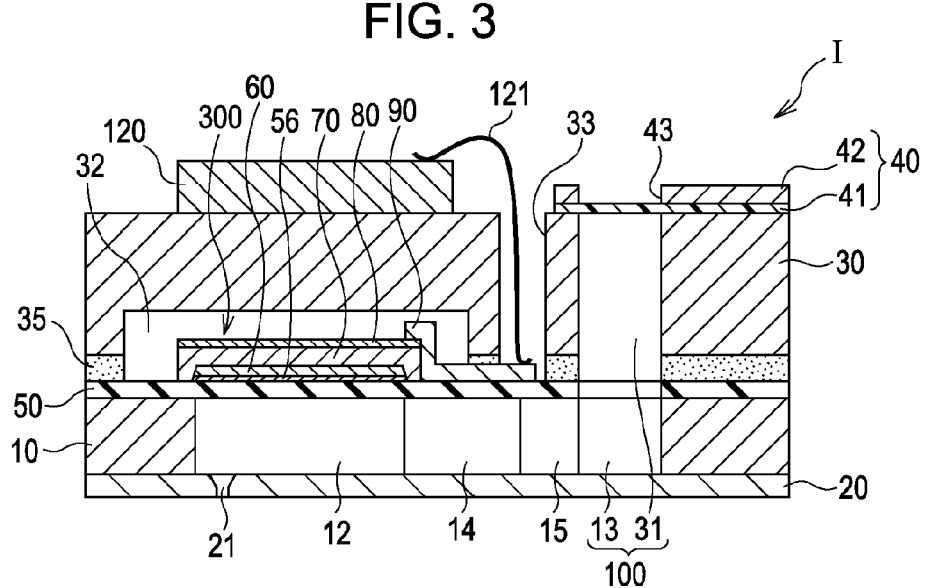
FIG. 3 is a sectional view of the recording head according to the embodiment.

FIG. 1 is a schematic exploded perspective view of an ink jet recording head, which is a type of liquid ejecting head, according to an embodiment of the invention. FIG. 2 is a plan view of FIG. 1, and FIG. 3 is a sectional view taken along line III-III shown in FIG. 2. As shown in FIGS. 1 to 3, a flow channel substrate 10 of the present embodiment is defined by a monocrystalline silicon substrate, and a silicon dioxide elastic film 50 is disposed on one surface of the flow channel substrate 10.

The flow channel substrate 10 has a plurality of pressure generating chambers 12 arranged in parallel in the width direction of the pressure generating chambers 12. The flow channel substrate 10 also has a communicating section 13 therein located outside the pressure generating chambers 12 in the longitudinal direction of the pressure generating chambers 12. The communicating section 13 communicates with the pressure generating chambers 12 through corresponding ink supply channels 14 and communication paths 15. The communicating section 13 communicates with a manifold section 31 formed in a below-described protective substrate to define a part of a manifold acting as a common ink chamber of the pressure generating chambers 12. Each ink supply channel 14 has a smaller width than the pressure generating chamber 12, so that the flow channel resistance of the ink delivered to the pressure generating chamber 12 from the communicating section 13 is kept constant. Although the ink supply channels 14 are formed by narrowing the flow channels from one side in the present embodiment, the flow channels may be narrowed from both sides in another embodiment. Alternatively, the ink supply channels 14 may be formed by reducing the depth of the flow channels, instead of narrowing the flow channels. In the present embodiment, the flow channel substrate 10 has liquid flow channels including the pressure generating chambers 12, the communicating section 13, the ink supply channels 14 and the communication paths 15.

The flow channel substrate 10 is joined to a nozzle plate 20 at the open side thereof with an adhesive, a thermal fusion film or the like. The nozzle plate 20 has nozzle apertures 21 communicating with portions around the ends of the corresponding pressure generating chambers 12 opposite to the ink supply channels 14. The nozzle plate 20 can be made of, for example, glass-ceramic, monocrystalline silicon or stainless steel.

On the opposite side to the open side of the flow channel substrate 10, the above-mentioned elastic film 50 is disposed, and an adhesion layer 56 having a thickness of, for example, about 30 to 50 nm and made of titanium oxide or the like is disposed on the elastic film 50 to enhance the adhesion between the elastic film 50 and the overlying first electrode 60. The elastic film 50 may be provided thereon with an insulating film made of zirconium oxide or the like, if necessary.

Furthermore, piezoelectric elements 300 are disposed on the adhesion layer 56. Each piezoelectric element 300 has a multilayer structure including a first electrode 60, a piezoelectric layer 70 having a small thickness of 0.7 to 3 µm, preferably 0.7 to 1.5 µm, and a second electrode 80. The piezoelectric element 300 acts as a pressure-generating device that changes the pressure in the corresponding pressure-generating chamber 12. The piezoelectric element 300 mentioned herein refers to the portion including the first electrode 60, the piezoelectric layer 70 and the second electrode 80. In general, one of the electrodes of the piezoelectric element 300 acts as a common electrode, and the other electrode and the piezoelectric layer 70 are formed for each pressure generating chamber 12 by patterning.

Although in the present embodiment, the first electrode 60 acts as the common electrode of the piezoelectric elements 300 and the second electrode 80 is provided as discrete electrodes of the piezoelectric elements 300, the functions of the first and second electrodes may be reversed for the sake of convenience of arrangement of the drive circuit and wiring. An actuator device mentioned herein is defined as a combination of the piezoelectric element 300 and a vibration plate that is displaced by the operation of the piezoelectric element 300. Although in the present embodiment, the elastic film 50, the adhesion layer 56 and the first electrode 60, and optionally an insulating film, act as a vibration plate, the vibration plate is not limited to this structure, and the elastic film 50 and the adhesion layer 56 are not necessarily provided. The piezoelectric element 300 may double as a vibration plate.

In the present embodiment, the piezoelectric layer 70 is made of a complex oxide containing bismuth (Bi), barium (Ba), iron (Fe) and titanium (Ti) and having a perovskite structure. In the complex oxide of the piezoelectric layer 70, the mole ratio (Ti/Ba) of Ti to Ba is larger than 1. Also, the mole ratio (Bi/Ba) of Bi to Ba is preferably in the range of 2.3 to 4.0. However, the complex oxide of the piezoelectric layer 70 is not limited to these mole ratios as long as the length of cracks extending from the four corners of an indentation, measured by a specific method described later is 15 µm or less. For example, the mole ratio (Ti/Ba) of Ti to Ba may be 1.

The complex oxide of the piezoelectric layer 70 has a perovskite structure, that is, an $ABO_3$ structure, as described above. The A site of this perovskite structure has 12 oxygen ligands, and the B site has 6 oxygen ligands to form an octahedron. The A site contains Bi and Ba, and the B site contains Fe and Ti.

In a typical complex oxide used in the present embodiment, the ratio (Bi+Ba):(Fe+Ti) of the total amount by mole of Bi and Ba to the total amount by mole of Fe and Ti may be 1:1. However, the composition of the complex oxide may be varied by lattice mismatch, oxygen defects and so forth, or part of one or more elements may be substituted, as long as the complex oxide has a perovskite structure. In the complex oxide of the present embodiment, the mole ratio (Ti/Ba) of Ti to Ba is larger than 1, as described above. Also, the mole ratio (Bi/Ba) of Bi to Ba is preferably in the range of 2.3 to 4.0. The composition of the complex oxide of the piezoelectric layer 70, having such a perovskite structure is expressed by the following General Formula (1). General Formula (1) expresses a composition based on the stoichiometry. As long as the complex oxide has a perovskite structure, the composition may be varied by lattice mismatch, oxygen defects and so forth, or part of one or more elements may be substituted, as described above.

$$(Bi_{1-a}Ba_a)(Fe_{1-b}Ti_b)O_3 \tag{1}$$

In General Formula (1), a and b satisfy the relationships b/a>1, and preferably satisfy the relationship $2.3 \le (1-a)/a \le 4.0$.

The complex oxide of the piezoelectric layer 70 may contain other elements in addition to Bi, Fe, Ba and Ti from the viewpoint of improving desired properties. For example, the complex oxide may contain one or both of Mn and Co. Even if the complex oxide contains such other elements, the complex oxide has a perovskite structure.

It is supposed that when the piezoelectric layer 70 contains Mn and Co, the complex oxide has a structure in which Mn and Co are located in the B site in such a manner that the Mn and Co substitute for part of the Fe in the B site. For example, when the complex oxide contains Mn, the fundamental characteristics of the complex oxide are the same as the complex oxide containing Bi, Fe, Ba and Ti and having a perovskite structure, and properties involved in leakage are improved. More specifically, the occurrence of leakage is suppressed. When the complex oxide contains Co, properties involved in leakage are improved as in the case where Mn is contained. In the above description, cases where the complex oxide contains Mn, Co or both are described by way of example. In addition, it has been known that the properties involved in the prevention of leakage can be improved in the case where one or more of other transition elements such as Cr, Ni and Cu are contained. Thus, the piezoelectric layer 70 may contain these elements, and may further contain other additives from the viewpoint of enhancing the properties.

In a typical composition of the complex oxide, the ratio of the total amount by mole of the A site to the total amount by mole of the B site may be 1:1. However, the composition of the complex oxide may be varied by lattice mismatch, oxygen defects and so forth, or part of one or more elements may be substituted, as long as the complex oxide has a perovskite structure. The piezoelectric layer 70 made of a complex oxide containing at least one of Mn, Co and other transition elements in addition to Bi, Fe, Ba and Ti and having a perovskite structure is a mixed crystal expressed by, for example, the following General Formula (2). In General Formula (2), M represents a transition element, such as Mn, Co, Cr, Ni, or Cu. General Formula (2) expresses a composition based on the stoichiometry. As long as the complex oxide has a perovskite structure, the composition may be varied by lattice mismatch, oxygen defects and so forth, as described above.

$$(Bi_{1-a}Ba_a)(Fe_{1-b-c}M_cTi_b)O_3 \quad (2)$$

In General Formula (2), a and b satisfy the relationships b/a>1, and preferably satisfy the relationship $2.3 \leq (1-a)/a \leq 4.0$. Also, c represents a number in the range of 0 to 0.09, preferably in the range of 0.01 to 0.05.

The piezoelectric layer 70 may contain another compound having a perovskite structure, such as Bi(Zn, Ti)O$_3$, (Bi, K)TiO$_3$, (Bi, Na)TiO$_3$, or (Li, Na, K)(Ta, Nb)O$_3$.

In the present embodiment, the piezoelectric layer 70 is made of a complex oxide containing Bi, Ba, Fe, Mn and Ti and having a perovskite structure, and the complex oxide is expressed by the following General Formula (3). General Formula (3) expresses a composition based on the stoichiometry. As long as the complex oxide has a perovskite structure, the composition may be varied by element diffusion, lattice mismatch, oxygen defects and so forth.

$$(Bi_{1-a}Ba_a)(Fe_{1-b-c}Mn_cTi_b)O_3 \quad (3)$$

In General Formula (3), a and b satisfy the relationships b/a>1, and preferably satisfy the relationship $2.3 \leq (1-a)/a \leq 4.0$. Also, c represents a number in the range of 0 to 0.09, preferably in the range of 0.01 to 0.05.

Although the piezoelectric material of the piezoelectric layer 70 of the present embodiment is a complex oxide containing Bi, Fe, Ba and Ti and having a perovskite structure, the piezoelectric material in another embodiment may be any one of other lead-free piezoelectric materials without particular limitation. Lead-free piezoelectric materials include barium titanate (BaTiO$_3$), bismuth ferrate (BiFeO$_3$), potassium sodium niobate ((K, Na)NbO$_3$), bismuth sodium titanate ((Bi$_{1/2}$Na$_{1/2}$)TiO$_3$), materials prepared by adding one or more elements to these piezoelectric materials, and complex oxides prepared by mixing these materials, materials containing these complex oxides, and Bi-layered compounds. Also, the piezoelectric layer 70 may be made of a lead-containing piezoelectric material, such as lead zirconate titanate (PbZrTiO$_3$).

Figure 4:
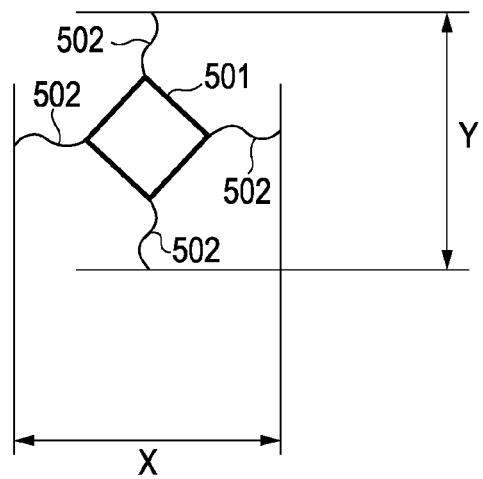
FIG. 4 is a representation of a method for measuring the length of cracks extending from the four corners of an indentation.

In any embodiment of the invention, the piezoelectric layer 70 made of a piezoelectric material is such that when a diamond conical indenter having an angle α of 136° between opposite faces is pressed into the piezoelectric layer 70 to form an indentation at a load of 5 gf for 5 seconds using a micro Vickers hardness meter, cracks will be formed from the indentation, and the length of the cracks from the four corners of the indentation is 15 μm or less. Such a piezoelectric layer 70 will now be described in detail with reference to FIG. 4. FIG. 4 is a representation of a method for measuring the length of cracks extending from the four corners of an indentation.

First, a diamond conical indenter having an angle α of 136° between opposite faces is pressed into the piezoelectric layer 70 at a load of 5 gf for 5 seconds using a micro Vickers hardness meter. Thus, cracks are formed from the four corners of the diamond conical indenter. After being pressed for 5 seconds as described above, the diamond conical indenter is removed from the piezoelectric layer 70. Thus, cracks 502 extending from the four corners of an indentation 501 are observed as shown in FIG. 4. In embodiments of the invention, the length of the cracks 502 from the four corners of the indentation 501 is 15 μm or less. The length of the cracks 502 from the four corners of the indentation 501 refers to the average of two lengths of the cracks extending nearly in the two diagonal directions. More specifically, in FIG. 4, the average of lengths X and Y is the length of the cracks from the four corner of the indentation 501. By forming the piezoelectric layer of a piezoelectric material such that the length of cracks 502 from the four corners of the indentation 501 will be 15 μm or less, the occurrence of cracks in the piezoelectric layer 70 can be suppressed.

The length of the cracks from the four corners of the indentation 501, measured by the above-described method has a high correlation with the occurrence of cracks in the piezoelectric layer 70. More specifically, for example, when the length of the cracks from the four corners of the indentation 501 measured by the above method is 15 μm or less, the number of cracks that will occur is very small. Therefore, how easily the piezoelectric layer 70 cracks can be simply evaluated by measuring the length of cracks 502 from the four corners of the indentation 501 by the above-described method. For example, when the length of cracks 502 from the four corners of an indentation 501 measured by the above method is 15 μm or less in a piezoelectric layer 70, it can be determined that the piezoelectric layer 70 does not substantially crack.

The Young's modulus, the hardness and other properties of the piezoelectric layer 70 are also involved with the occurrence of cracks. However, as will be shown in the Examinations described below, even though piezoelectric layers have the same Young's modulus, cracks may or may not occur. Also, even in a piezoelectric layer having a low Young's modulus, a crack may easily occur. Thus, there is no correlation between the occurrence of cracks and the Young's modulus of the piezoelectric layer 70. In a process for forming a piezoelectric layer by a sol-gel method, as disclosed in JP-A-2001-19543, the ratio of the Vickers hardness of a piezoelectric film after being dried and degreased to the Vickers hardness of the film after being further fired may be controlled to 0.1 or less. However, it is very difficult to measure the Vickers hardness of a dried and degreased film. Accordingly, it is not easy to evaluate how easily the piezoelectric layer 70 cracks on the basis of the hardness of the dried and degreased film.

Since the length of the cracks 502 from the four corners of an indentation 501, measured by the above method has a high correlation with the occurrence of cracks in the piezoelectric layer 70, how easily the piezoelectric layer 70 cracks can be accurately evaluated by measuring the length of the cracks 502 from the four corners of the indentation 501.

Since a piezoelectric layer 70 into which a diamond conical indenter has been pressed for the above-described measurement has an indentation 501 and cracks 502 therein, the piezoelectric layer 70 is not used as a component of an ink jet recording head. In a practical process for manufacturing an ink jet recording head on part of a silicon wafer or any other wafer, as will be described in a manufacturing method below, the measurement of the length of cracks can be performed such that after piezoelectric layers 70 are formed at one time over the entire surface of the wafer under the same conditions, cracks 502 extending from an indentation 501 are formed in a piezoelectric layer located at an end of the arrangement of the piezoelectric layers 70 and exposed without being covered with the second electrode 80 or by removing the second electrode 80, and the length of the cracks 502 from the four corners of the indentation is measured by the above method. In this instance, the indentation 501 or cracks 502 formed for the measurement may remain in the ink jet recording head. Of course, the cracks 502 may be formed for the measurement in a piezoelectric layer that is located at an end of the wafer and will be removed by dicing or the like and thus not be used for the ink jet recording head. Alternatively, piezoelectric layers may be formed under various conditions, and the length of cracks 502 from the four corners of an indentation 501 is measured for each of the piezoelectric layers by the above method in advance. Then, piezoelectric layers 70 that will be used in the ink jet recording head are formed under the same conditions as the piezoelectric layer in which the cracks 502 has had a length of 15 μm or less from the four corners of the indentation 501.

The length of the cracks 502 from the four corners of the indentation 501, measured by the above method is varied depending on various factors such as the constituents and their proportions in the piezoelectric material, the firing temperature and other conditions for forming the piezoelectric layer 70, and the Young's modulus, hardness and thickness of the piezoelectric layer 70. The length of the cracks 502 from the four corners of the indentation 501 measured by the above method can be controlled to 15 μm or less by adjusting the balance of those factors.

In the present embodiment, the piezoelectric layer 70 may be oriented in the (110), (100) or (111) plane without particular limitation.

The second electrode 80 provided for each piezoelectric element 300 is connected to a lead electrode 90 made of, for example, gold (Au). The lead electrode 90 extends from the end of the second electrode 80 near the ink supply channel 14 to the upper surface of the elastic film 50 and, optionally, to the upper surface of an insulating film.

A protective substrate 30 having a manifold section 31 defining at least part of a manifold 100 is joined to the flow channel substrate 10 having the piezoelectric elements 300 with an adhesive 35 so as to cover the first electrode 60, the elastic film 50, an optionally provided insulating film, and the lead electrodes 90. The manifold section 31 passes through the protective substrate 30 in the thickness direction and extends along the widths of the pressure generating chambers 12. Thus, the manifold section 31 communicates with the communicating section 13 of the flow channel substrate 10 to form the manifold 100 that will act as the common ink chamber of the pressure generating chambers 12. The communicating section 13 of the flow channel substrate 10 may be divided for each pressure generating chamber 12, and only the manifold section 31 may serve as the manifold. The flow channel substrate 10 may have only the pressure generating chambers 12, and ink supply channels 14 communicating between the manifold 100 and the pressure generating chambers 12 are formed in a member between the flow channel substrate 10 and the protective substrate 30, such as the elastic film 50 and an optionally provided insulating film.

A piezoelectric element-protecting section 32 is disposed in the region of the protective substrate 30 opposing the piezoelectric elements 300. The Piezoelectric element-protecting section 32 has a space so that the piezoelectric elements 300 can operate without interference. The space of the piezoelectric element-protecting section 32 is intended to ensure the operation of the piezoelectric elements 300, and may or may not be sealed.

Preferably, the protective substrate 30 is made of a material having substantially the same thermal expansion coefficient as the flow channel substrate 10, such as glass or ceramic. In the present embodiment, the protective substrate 30 is made of the same monocrystalline silicon as the flow channel substrate 10.

The protective substrate 30 has a through hole 33 passing through the protective substrate 30 in the thickness direction. The ends of the lead electrodes 90 extending from the piezoelectric elements 300 are exposed in the through hole 33.

A drive circuit 120 is secured on the protective substrate 30 and drives the piezoelectric elements 300 arranged in parallel. The drive circuit 120 may be a circuit board, a semiconductor integrated circuit (IC) or the like. The drive circuit 120 is electrically connected to each lead electrode 90 with a conductive connection wire 121, such as bonding wire.

Furthermore, a compliance substrate 40 including a sealing film 41 and a fixing plate 42 is joined on the protective substrate 30. The sealing film 41 is made of a flexible material having a low rigidity, and seals one end of the manifold section 31. The fixing plate 42 is made of a relatively hard material. The portion of the fixing plate 42 opposing the manifold 100 is completely removed to form an opening 43; hence the manifold 100 is closed at one end only with the flexible sealing film 41.

The ink jet recording head I of the present embodiment draws an ink through an ink inlet connected to an external ink supply unit (not shown). The ink is delivered to fill the spaces from the manifold 100 to the nozzle apertures 21. Then, the ink jet recording head I applies a voltage between the first electrode 60 and each second electrode 80 corresponding to the pressure generating chambers 12, according to the recording signal from the driving circuit 120. Thus, the elastic film 50, the adhesion layer 56, the first electrode 60 and the piezoelectric layers 70 are deformed to increase the internal pressure in the pressure generating chambers 12, thereby discharging the ink through the nozzle apertures 21.

A method for manufacturing the ink jet recording head according to the present embodiment will be described with reference to FIGS. 5A to 9B. FIGS. 5A to 9B are sectional views of the pressure generating chamber taken in the longitudinal direction.

Figure 5A:
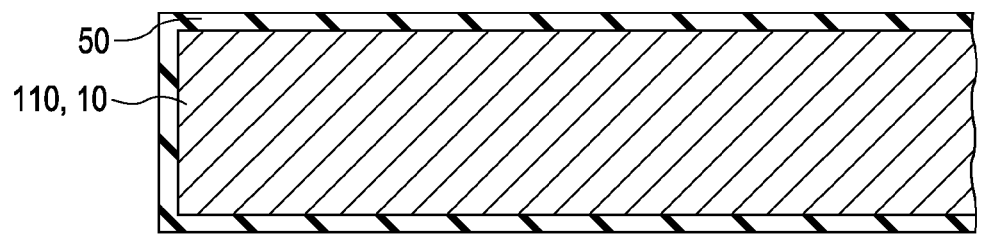
FIGS. 5A and 5B are sectional views showing a process for manufacturing the recording head according to the embodiment.

As shown in FIG. 5A, a silicon dioxide ($SiO_2$) film is formed for an elastic film 50 on the surface of a flow channel substrate silicon wafer 110 by, for example, thermal oxidation. If an insulating film (not shown) of zirconium oxide or the like is formed on the elastic film 50, the insulating film can be formed by, for example, reactive sputtering or thermal oxidation.

Figure 5B:
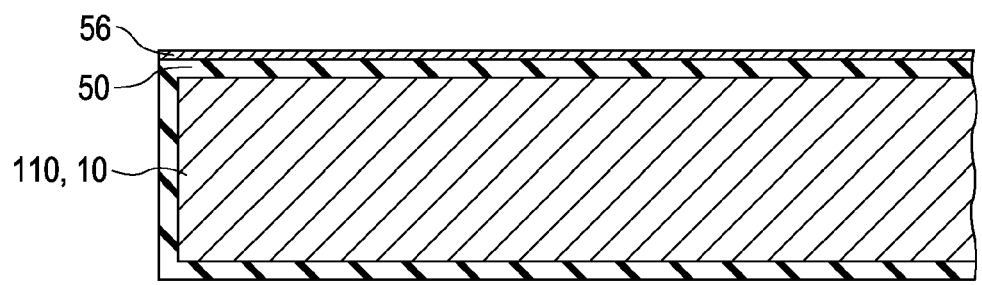

Subsequently, an adhesion layer 56 is formed of titanium oxide or the like on the elastic film 50 (silicon dioxide film), or on the insulating film if provided, by sputtering, thermal oxidation or the like, as shown in FIG. 5B.

Figure 6A:
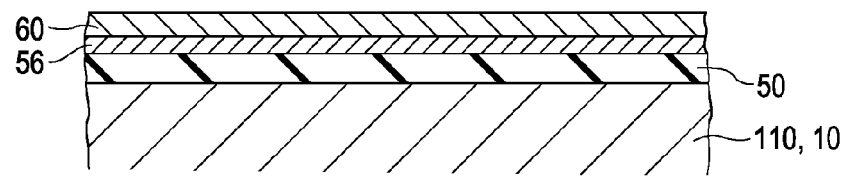
FIGS. 6A to 6C are sectional views showing the process for manufacturing the recording head according to the embodiment.
Figure 6B:
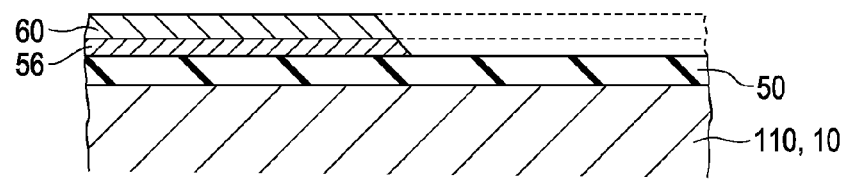

Subsequently, a first electrode 60 made of platinum, iridium, iridium oxide, or a multilayer structure of these materials is formed over the entire surface of the adhesion layer 56 by sputtering, vapor deposition or the like, as shown in FIG. 6A. Then, the first electrode 60 and the adhesion layer 56 are simultaneously patterned so that their sides are inclined, using as a mask a resist layer (not shown) having a predetermined shape and disposed on the first electrode 60, as shown in FIG. 6B.

Then, after removing the resist layer, piezoelectric layers 70 are formed on the first electrode 60. The piezoelectric layers may be formed any method without particular limitation, as long as the resulting piezoelectric layers 70 are such that when a diamond conical indenter having an angle α of 136° between opposite faces is pressed into the piezoelectric layer to form cracks extending from an indentation at a load of 5 gf for 5 seconds using a micro Vickers hardness meter, the length of the cracks from the four corners of the indentation will be 15 μm or less. For example, the piezoelectric layers 70 may be formed by metal organic decomposition (MOD), in which a metal oxide piezoelectric layer (piezoelectric film) is formed by applying a metal complex solution, drying the coating of the metal complex solution and then firing the coating at a high temperature, or by any other chemical solution method such as a sol-gel method. The piezoelectric layer 70 can be formed by other methods, such as laser ablation, sputtering, pulsed laser deposition (PLD), CVD or aerosol deposition, irrespective of liquid phase process or solid phase process.

Figure 6C:
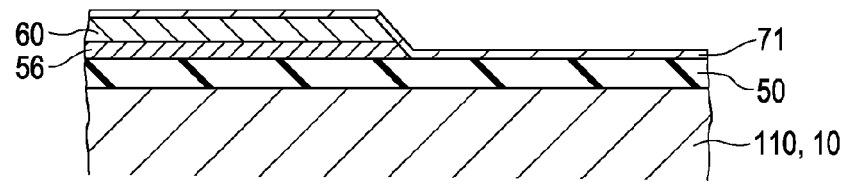

For example, in an embodiment in which the piezoelectric layer 70 is formed by a chemical solution method, first, a piezoelectric film-forming composition (precursor solution) containing a metal complex is applied onto the first electrode 60 by spin coating or the like to form a piezoelectric precursor film 71, as shown in FIG. 6C (coating step). In the present embodiment, the precursor solution may be an MOD solution or a sol that contains metal complexes containing Bi, Fe, Ba and Ti.

The precursor solution is prepared by dissolving or dispersing in an organic solvent a mixture of metal complexes that will form a complex oxide of the piezoelectric layer 70 by firing. In the present embodiment, metal complexes are used which will form a complex oxide containing Bi, Fe, Ba and Ti by firing and thus form the piezoelectric layer 70. If a piezoelectric layer 70 made of a complex oxide further containing Mn, Co or Cr is formed, the precursor solution further contains a metal complex containing Mn, Co or Cr. The metal complexes are mixed in a proportion in which each metal element will have a desired mole ratio. More specifically, in the present embodiment, the metal complexes are mixed in such a proportion that the resulting complex oxide will have a Ti/Ba mole ratio of more than 1 and, preferably, a Bi/Ba mole ratio of 2.3 to 4.0. The metal complexes include alkoxides, organic acid salts, and β-diketone complexes. Examples of the metal complex containing Bi include bismuth 2-ethylhexanoate and bismuth acetate. Examples of the metal complex containing Fe include iron 2-ethylhexanoate, iron acetate, and iron tris(acetylacetonate). Examples of the metal complex containing Ba include barium isopropoxide, barium 2-ethylhexanoate, and barium acetylacetonate. Examples of the metal complex containing Ti include titanium isopropoxide, titanium 2-ethylhexanoate, and titanium diisopropoxide bis(acetylacetonate). Examples of the metal complex containing Mn include manganese 2-ethylhexanoate and manganese acetate. Examples of the metal complex containing Co include cobalt 2-ethylhexanoate and cobalt (III) acetylacetonate. The organic metal compound containing Cr may be chromium 2-ethylhexanoate. Metal complexes containing two or more metals may be used. Examples of the solvent in the precursor solution include propanol, butanol, pentanol, hexanol, octanol, ethylene glycol, propylene glycol, octane, decane, cyclohexane, xylene, toluene, tetrahydrofuran, acetic acid, and octylic acid.

Subsequently, the piezoelectric precursor film 71 is dried for a certain time by being heated to a predetermined temperature (for example, 130 to 200° C.) (drying step). Then, the dried piezoelectric precursor film 71 is degreased by being heated to a predetermined temperature (for example, 350 to 450° C.) and allowed to stand at that temperature for a certain time (degreasing step). The degreasing mentioned herein is performed to convert organic components in the piezoelectric precursor film 71 into, for example, $NO_2$, $CO_2$ or $H_2O$ and thus to remove the organic components. The drying and degreasing may be performed in any atmosphere without particular limitation, and may be performed in the air, an oxygen atmosphere or an inert gas atmosphere. The steps of coating, drying and degreasing may be repeated.

Figure 7A:
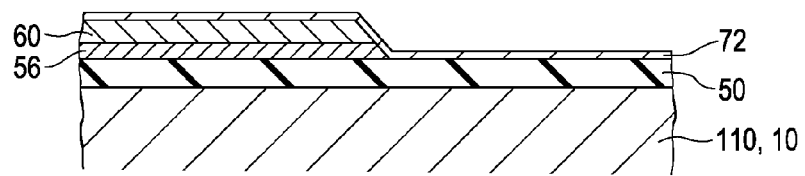
FIGS. 7A and 7B are sectional views showing the process for manufacturing the recording head according to the embodiment.

Subsequently, as shown in FIG. 7A, the piezoelectric precursor film 71 is crystallized by being heated to a predetermined temperature, such as about 600 to 850° C., and keeping that temperature for a certain time, such as for 1 to 10 minutes. Thus, a piezoelectric film 72 is formed which is made of a complex oxide having a perovskite structure and containing Bi, Ba, Fe and Ti, in a Ti/Ba mole ratio of more than 1 in the present embodiment (firing step). The firing step may be performed in any atmosphere without particular limitation, and may be performed in the air, an oxygen atmosphere or an inert gas atmosphere. The heating apparatus used in the steps of drying, degreasing and firing may be an RTA (Rapid Thermal Annealing) apparatus using an infrared lamp for heating, or a hot plate.

Figure 7B:
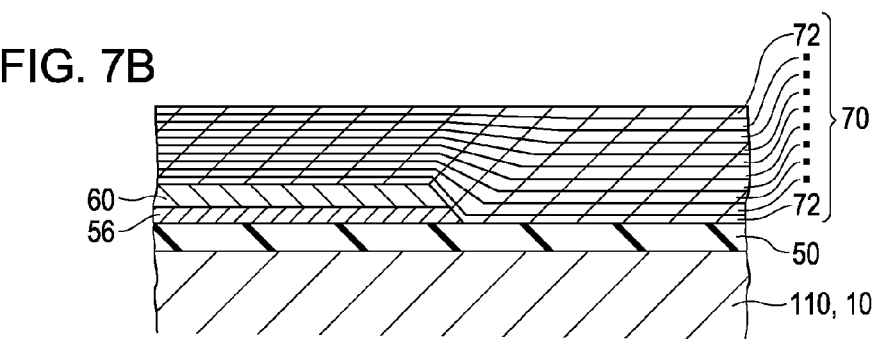

The steps of coating, drying and degreasing, or the steps of coating, drying, degreasing and firing are repeated several times according to the desired thickness, thus forming a plurality of piezoelectric films 72. Thus, the piezoelectric layer 70 including the piezoelectric films 72 is formed to a predetermined thickness, as shown in FIG. 7B. For forming the piezoelectric films 72, the operations of coating, drying, degreasing and firing may be performed step by step, or the firing step may be performed at one time after the sequence of the steps of coating, drying and degreasing has been repeated. Although piezoelectric films 72 are formed on top of one another in the present embodiment, the piezoelectric layer 70 may include only a single piezoelectric film 72 in another embodiment.

As described above, the length of the cracks 502 from the four corners of an indentation 501 can be controlled by adjusting the constituents and their proportions in the precursor solution, the firing temperature and other firing conditions for firing the piezoelectric layer 70, the thickness of the piezoelectric layer 70, and other factors. Since the length of the cracks 502 from the four corners of the indentation 501 is varied depending on each of the constituents and their proportions in the precursor solution, the firing temperature and other firing conditions for firing the piezoelectric layer 70, and the thickness of the piezoelectric layer 70, the balance among these conditions or factors is appropriately adjusted.

Figure 8A:
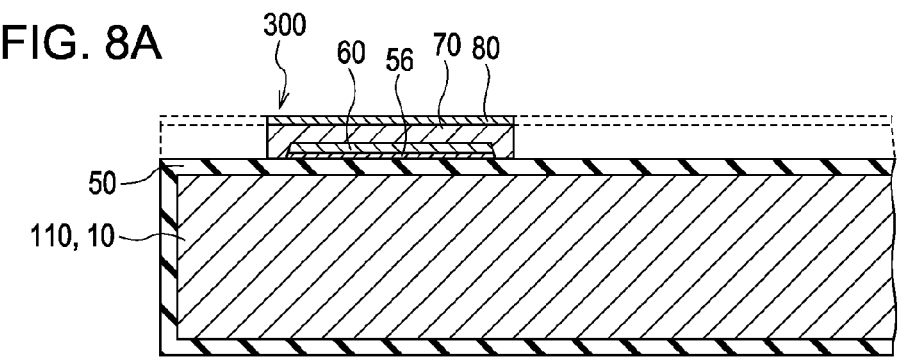
FIGS. 8A to 8C are sectional views showing the process for manufacturing the recording head according to the embodiment.

After the piezoelectric layer 70 is formed, a second electrode 80 is formed of platinum or the like on the piezoelectric layer 70 by, for example, sputtering, and the piezoelectric layer 70 and the second electrode 80 are simultaneously patterned so as to form piezoelectric elements 300, each including the first electrode 60, the piezoelectric layer 70 and the second electrode 80, in regions corresponding to the pressure generating chambers 12, as shown in FIG. 8A. The patterning of the piezoelectric layer 70 and the second electrode 80 can be performed at one time by dry etching through a resist layer (not shown) having a predetermined shape. After this operation, post-annealing may be performed at a temperature in the range of 600 to 800° C., if necessary. Thus, satisfactory interfaces can be formed between the piezoelectric layer 70 and the first electrode 60 and between the piezoelectric layer 70 and the second electrode 80, and, in addition, the crystallinity of the piezoelectric layer 70 can be enhanced.

Figure 8B:
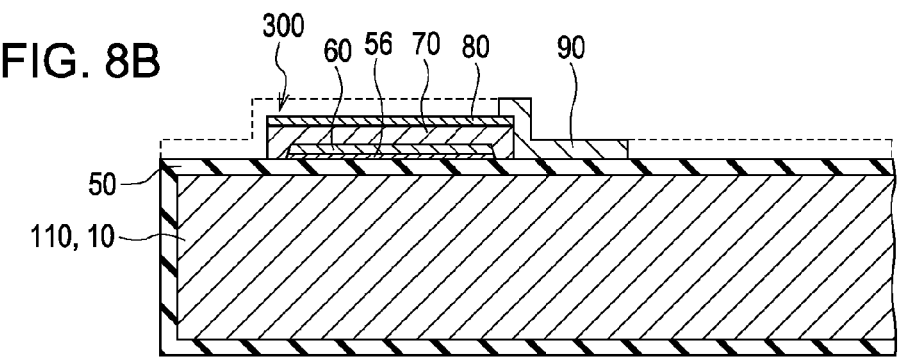

Then, a film is formed of, for example, gold (Au), over the entire surface of the flow channel substrate wafer 110, and is patterned into lead electrodes 90 for the respective piezoelectric elements 300, as shown in FIG. 8B, through a mask pattern (not shown) made of, for example, resist.

Figure 8C:
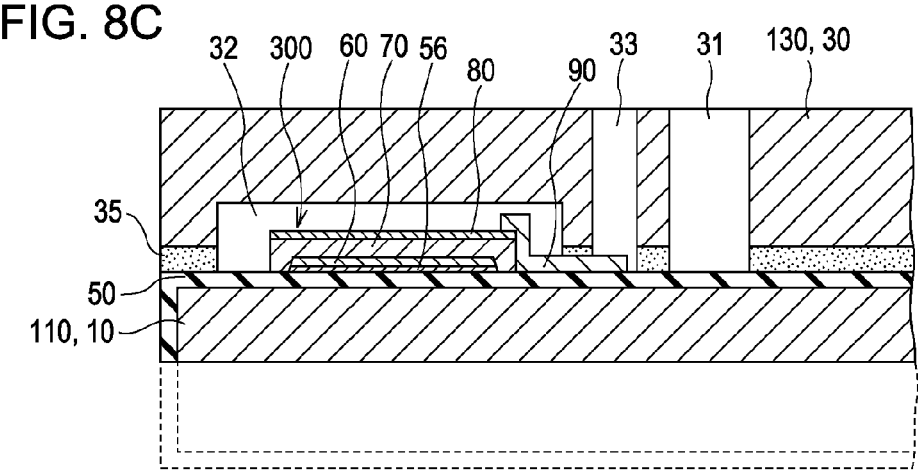

Then, a silicon protective substrate wafer 130 for a plurality of protective substrates 30 is bonded to the surface of the flow channel substrate wafer 110 having the piezoelectric elements 300 with an adhesive 35, and the thickness of the flow channel substrate wafer 110 is reduced to a predetermined level, as shown in FIG. 8C.

Figure 9A:
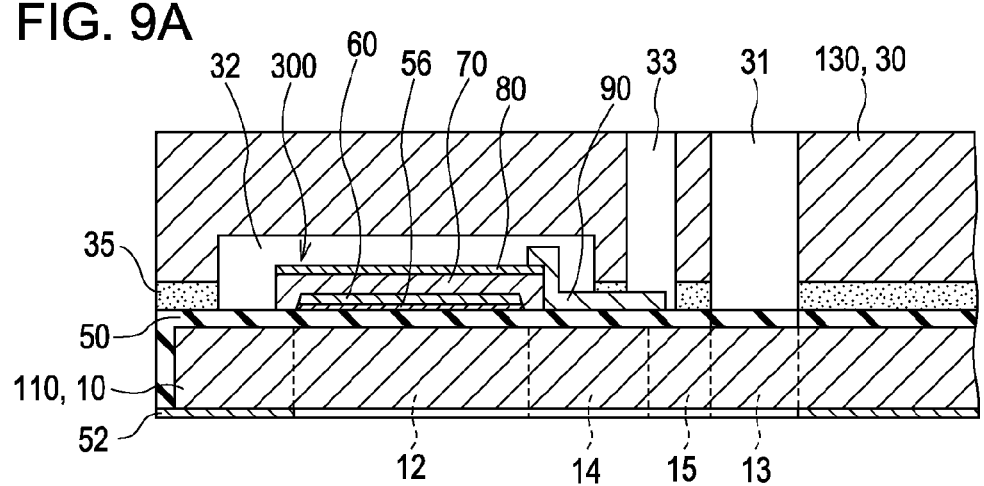
FIGS. 9A and 9B are sectional views showing the process for manufacturing the recording head according to the embodiment.

Then, as shown in FIG. 9A, a mask layer is formed on the surface of the flow channel substrate wafer 110 opposite the protective substrate wafer 130 and is patterned into a mask 52 having a predetermined shape.

Figure 9B:
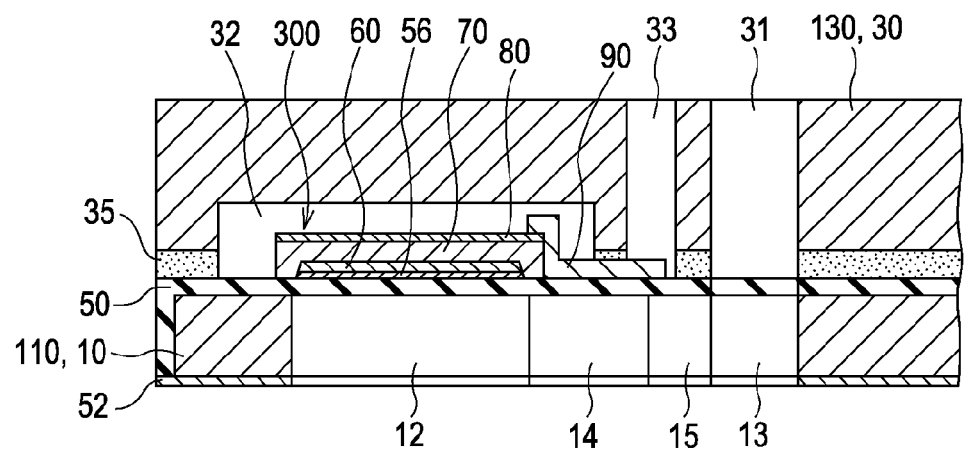

Subsequently, as shown in FIG. 9B, the flow channel substrate wafer 110 is subjected to anisotropic etching (wet etching) using an alkaline solution, such as KOH, through the mask 52 to form the pressure generating chambers 12 corresponding to the piezoelectric elements 300, the communicating section 13, the ink supply channels 14 and the communication paths 15 therein.

Then, unnecessary outer portions of the flow channel substrate wafer 110 and protective substrate wafer 130 are cut off by, for example, dicing. Subsequently, a nozzle plate 20 having nozzle apertures 21 therein is joined to the surface of the flow channel substrate wafer 110 opposite the protective substrate wafer 130 after the mask 52 has been removed, and a compliance substrate 40 is joined to the protective substrate wafer 130. The flow channel substrate wafer 110 joined to other substrates is cut into chips as shown in FIG. 1, each including a flow channel substrate 10 and other members. Thus, the ink jet recording head I of the present embodiment is completed.

EXAMPLES

The invention will be further described in detail with reference to Examples below. However, the invention is not limited to the following Examples.

Example 1

Preparation of Sample 1

First, a silicon dioxide film was formed to a thickness of 1170 nm on a (110)-oriented monocrystalline silicon substrate by thermal oxidation. Subsequently, a titanium film was formed to a thickness of 20 nm on the silicon dioxide film by RF magnetron sputtering, and was then thermally oxidized to form a titanium oxide film. Then, a platinum film was formed to a thickness of 130 nm on the titanium oxide film by RF magnetron sputtering, thus forming a first electrode 60.

A precursor solution was prepared by mixing solutions of bismuth 2-ethylhexanoate, barium 2-ethylhexanoate, iron 2-ethylhexanoate, manganese 2-ethylhexanoate and titanium 2-ethylhexanoate, each in n-octane, in a mole ratio of Bi:Ba:Fe:Mn:Ti=0.75:0.25:0.713:0.038:0.25.

The precursor solution was dropped onto the surface of the substrate on which the titanium oxide film and the first electrode 60 had been formed. The substrate was then subjected to spin coating at a rotation speed of 500 rpm for 5 seconds and subsequently at a rotation speed of 3000 rpm for 20 seconds, thus forming a piezoelectric precursor film (coating step). Then, the piezoelectric precursor film on the substrate was dried on a hot plate at 180° C. for 3 minutes (drying step). The piezoelectric precursor film was further subjected to degreasing on a hot plate at 350° C. for 3 minutes (degreasing step). The sequence of the steps of coating, drying and degreasing was performed three times, and, then, the resulting precursor films were fired at 800° C. for 5 minutes in an oxygen atmosphere using an RTA apparatus (firing step).

Subsequently, such an operation was repeated four times, and thus a piezoelectric layer 70 having a thickness of 1080 nm was formed by 12 coating operations in total.

Then, an iridium film having a thickness of 50 nm was formed as second electrodes 80 on the piezoelectric layer 70 by DC sputtering, and was then fired at 750° C. for 5 minutes by RTA to complete Sample 1 of the piezoelectric element. The mole ratio of the metal elements, the firing temperature and the thickness of the piezoelectric layer 70 are shown in the Table.

Examples 2 to 4

Preparation of Samples 2 to 4

Each sample was prepared in the same manner as in Example 1, except that firing was performed at the temperature shown in the Table.

Examples 5 to 11

Each sample was formed in the same manner as in Example 1, except that the mole ratio of Bi, Ba, Fe, Mn and Ti in the composition was set as shown in the Table.

Examination 1

Samples 1 to 11 of the piezoelectric element were subjected to X-ray diffraction analysis to obtain the diffraction pattern of the piezoelectric layer with D8 Discover (manufactured by Bruker AXS) using CuKα rays at room temperature. Peaks derived from the perovskite structure and the substrate were observed in all of Samples 1 to 11. More specifically, a peak of the (100) plane of the piezoelectric layer formed of a single phase of a perovskite structure was observed around 23°, a peak of the (110) plane of the silicon substrate was observed around 32°, and a peak of the (111) plane of Pt was observed around 40°. No heterogenous phase was observed.

Examination 2

For Samples 1 to 11, the Young's modulus of the piezoelectric layer 70 was measured with a nano indenter (UMIS 2000 manufactured by CSIRO) under the following conditions immediately after being formed and before the formation of the second electrodes 80. The results are shown in the Table.

Spherical indenter: has a diameter of 1 μm LA
Initial contact load: 0.03 mN
Maximum load: 0.5 mN
Load/Unload Increments: 20 (Linear)
Unloading to: 70% of maximum
Enable unload on increments: Unload Increments 1
Dwell: 1 s
Indent Delay: 30 s Examination 3

For Samples 1 to 11, a diamond conical indenter having an angle α of 136° between opposite faces was pressed into the piezoelectric layer 70 immediately after being formed and before the formation of the second electrodes 80 at a load of 5 gf for 5 seconds, using a micro Vickers hardness meter MVK-H 300 manufactured by Akashi. After being pressed for 5 seconds as described above, the diamond conical indenter was removed from the piezoelectric layer. Thus, cracks 502 extending from the four corners of the indentation 501 formed with the indenter were observed as shown in FIG. 4. Lengths X and Y, each of which is a length of two cracks 502 extending in one of the two diagonal directions as shown in FIG. 4, were measured. This sequence of operations for indentation and measurement, pressing the diamond conical indenter to form cracks 502 at a load of 5 gf for 5 seconds using the micro Vickers hardness meter and measuring the lengths of the cracks 502 extending in two diagonal directions from the four corners of the indentation 501, was performed 12 times. The largest Length X and the smallest Length X were omitted from the Lengths X of 12 measurements, and the average of Length X was calculated from the 10 Lengths X. Similarly, the largest Length Y and the smallest Length Y were omitted from the Lengths Y of 12 measurements, and the average of Length Y was calculated from the 10 Lengths Y. The average (X+Y)/2 of the average of Length X and the average of Length Y was defined as the length of the cracks 502 from the four corners of the indentation 501. The results of measurements for the length of cracks are shown in the Table.

Examination 4

For Samples 1 to 11, it was checked five days after Examination 3 whether or not the piezoelectric layer 70 was cracked in the region where the indentations 501 were not formed. The surface of the piezoelectric layer 70 was observed through a metallurgical microscope at a magnification of 500 times. The results are shown in the Table. When "Yes" is shown in the Table, one or more cracks were observed in the sample; when "No" is shown in the Table, no crack was observed in the sample.

In the results, even though the piezoelectric layers had the same Young's modulus, one piezoelectric layer cracked and another did not crack, as shown in Samples 7 and 8. Also, even though the Young's modulus was small, cracks occurred in some samples as in Samples 8 and 9. This shows that there is no correlation between the occurrence of cracks in a piezoelectric layer and the Young's modulus of the piezoelectric layer. On the other hand, it has been shown that when the length, measured by the above-described method, of cracks 502 from the four corners of an indentation 501 is 15 μm or less, no cracks occurred in the piezoelectric layer even after five days had elapsed.

TABLE 1

| | Mole ratio | | | | | Firing temperature | Thickness | Length of cracks | Young's modulus | Occurrence of cracks |
|---|---|---|---|---|---|---|---|---|---|---|
| | Bi | Ba | Fe | Mn | Ti | (° C.) | (nm) | (μm) | (Gpa) | after 5 days |
| Sample 1 | 0.750 | 0.250 | 0.713 | 0.038 | 0.250 | 800 | 1080 | 15.1 | 135 | Yes |
| Sample 2 | 0.750 | 0.250 | 0.713 | 0.038 | 0.250 | 750 | 800 | 16.4 | 136 | Yes |
| Sample 3 | 0.750 | 0.250 | 0.713 | 0.038 | 0.250 | 700 | 880 | more than 35.0 | 139 | Yes |
| Sample 4 | 0.750 | 0.250 | 0.713 | 0.038 | 0.250 | 650 | 800 | more than 35.0 | 142 | Yes |
| Sample 5 | 0.750 | 0.250 | 0.683 | 0.015 | 0.303 | 800 | 800 | 12.4 | 121 | No |
| Sample 6 | 0.750 | 0.250 | 0.668 | 0.015 | 0.318 | 800 | 850 | 13.1 | 119 | No |
| Sample 7 | 0.750 | 0.250 | 0.653 | 0.015 | 0.333 | 800 | 850 | 14.7 | 118 | No |
| Sample 8 | 0.700 | 0.300 | 0.623 | 0.014 | 0.363 | 800 | 850 | 24.38 | 118 | Yes |
| Sample 9 | 0.725 | 0.275 | 0.645 | 0.015 | 0.340 | 800 | 850 | 16.6 | 123 | Yes |
| Sample 10 | 0.775 | 0.225 | 0.690 | 0.016 | 0.295 | 800 | 850 | 10 | 119 | No |
| Sample 11 | 0.800 | 0.200 | 0.712 | 0.016 | 0.272 | 800 | 850 | 8.1 | 133 | No |

Other Embodiments

Although an exemplary embodiment of the invention has been described, the invention is not limited to the disclosed embodiment. For example, in the above embodiment, a monocrystalline silicon substrate is used as the flow channel substrate 10. However, the flow channel substrate 10 may be made of, for example, silicon-on-insulator (SOI) or glass, without particular limitation.

Also, although the piezoelectric element 300 of the above embodiment includes the first electrode 60, the piezoelectric layer 70 and the second electrode 80 that are stacked in that order on a substrate (flow channel substrate 10), the structure of the piezoelectric element is not limited to this structure. For example, an embodiment of the invention can be applied to a vertical vibration piezoelectric element including layers of a piezoelectric material and an electrode material alternately formed so as to expand and contract in the axis direction.

Figure 10:
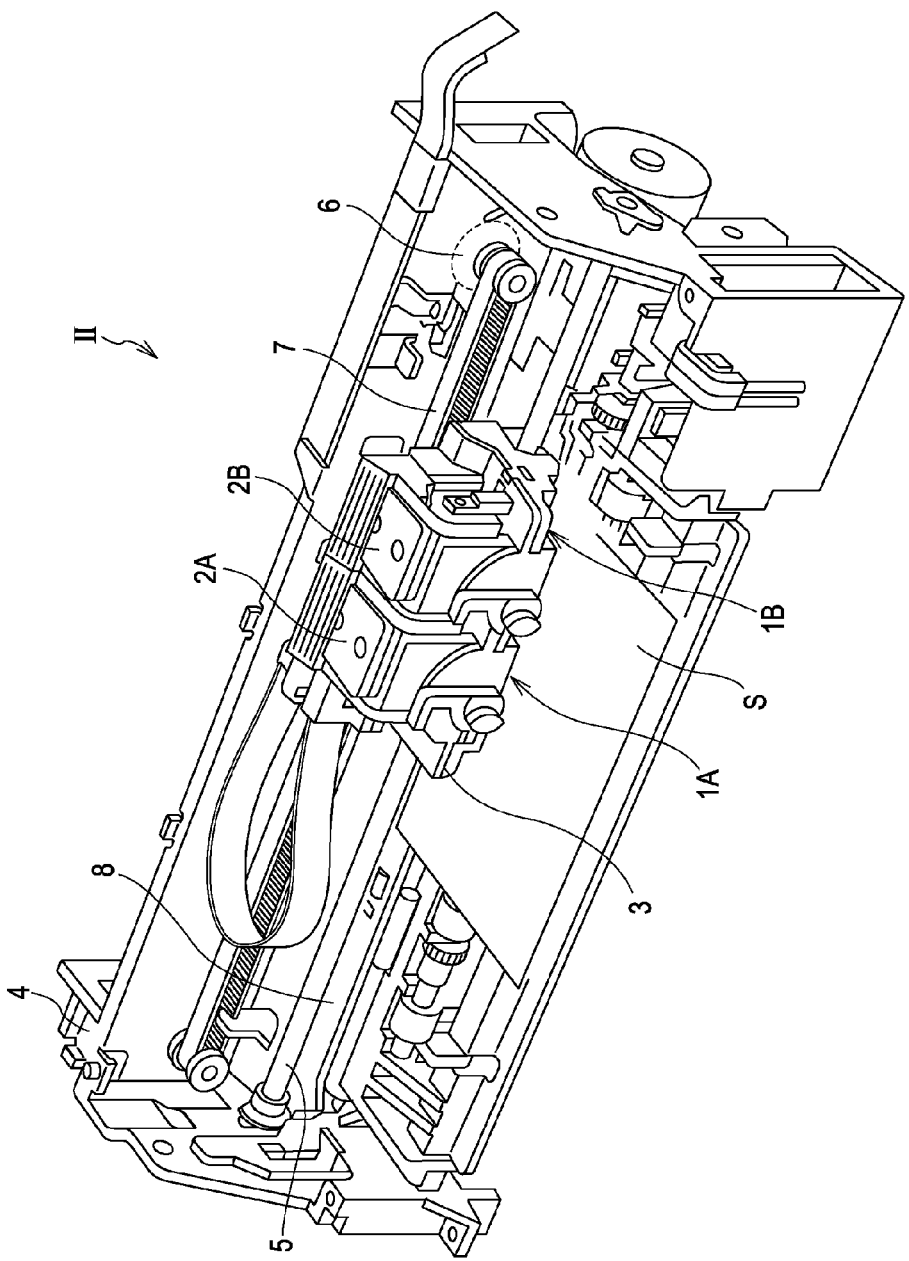
FIG. 10 is a schematic view of a recording apparatus according to an embodiment of the invention.

The ink jet recording head according to an embodiment of the invention can be installed in an ink jet recording apparatus to serve as a part of a recording head unit including ink flow channels communicating with an ink cartridge or the like. FIG. 10 is a schematic perspective view of such an ink jet recording apparatus.

The ink jet recording apparatus II shown in FIG. 10 includes recording head units 1A and 1B each including the ink jet recording head I, and cartridges 2A and 2B for supplying ink are removably mounted in the respective recoding head units 1A and 1B. The recording head units 1A and 1B are loaded on a carriage 3 secured for movement along a carriage shaft 5 of an apparatus body 4. The recording head units 1A and 1B discharge, for example, a black ink composition and a color ink composition, respectively.

The carriage 3 on which the recording head units 1A and 1B are mounted is moved along the carriage shaft 5 by transmitting a driving force from a driving motor 6 to the carriage 3 through a plurality of gears (not shown) and a timing belt 7. In the apparatus body 4, a platen 8 is disposed along the carriage shaft 5 so that a recording sheet S, which is a recording medium such as a paper sheet, fed from, for example, a feed roller (not shown), is transported over the platen 8.

Although the above embodiment has described an ink jet recording head as the liquid ejecting head, the invention is intended for any type of liquid ejecting head, and may be applied to other liquid ejecting heads that eject liquid other than ink. Other liquid ejecting heads include various types of recording head used in image recording apparatuses such as printers, color material ejecting heads used for manufacturing color filters of liquid crystal displays or the like, electrode material ejecting heads used for forming electrodes of organic EL displays or field emission displays (FEDs), and bioorganic material ejecting heads used for manufacturing biochips.

Also, the piezoelectric element according to embodiments of the invention is not limited to the piezoelectric element used for liquid ejecting heads, and can be used in other devices. Examples of such other devices include ultrasonic devices such as an ultrasonic oscillator, an ultrasonic motor, a temperature-electricity converter, a pressure-electricity converter, a ferroelectric transistor, a piezoelectric transformer, and filters, such as a cutoff filter for harmful rays such as infrared radiation, an optical filter using the photonic crystal effect of quantum dot formation, and an optical filter using optical interference of a thin film. The invention is also applied to a piezoelectric element used as a sensor and a piezoelectric element used as a ferroelectric memory. Sensors using a piezoelectric element include, for example, an infrared sensor, a supersonic sensor, a thermal sensor, a pressure sensor, a pyroelectric sensor, and a gyro sensor (angular velocity sensor).

What is claimed is:

1. A liquid ejecting head comprising:
a piezoelectric element including a piezoelectric layer made of a piezoelectric material and an electrode disposed on the piezoelectric layer,
wherein the piezoelectric material is such that when a diamond conical indenter having an angle of 136° between opposite faces is pressed into the piezoelectric layer at a load of 5 gf for 5 seconds to form cracks extending from an indentation, using a micro Vickers hardness meter, the length of the cracks from four corners of the indentation is 15 μm or less.

2. The liquid ejecting head according to claim 1, wherein the piezoelectric material is a complex oxide having a perovskite structure and containing bismuth, iron, barium and titanium.

3. A liquid ejecting apparatus comprising the liquid ejecting head as set forth in claim 1.

4. A liquid ejecting apparatus comprising the liquid ejecting head as set forth in claim 2.

5. A piezoelectric element comprising:
a piezoelectric layer made of a piezoelectric material; and
an electrode disposed on the piezoelectric layer,
wherein the piezoelectric material is such that when a diamond conical indenter having an angle of 136° between opposite faces is pressed into the piezoelectric layer at a load of 5 gf for 5 seconds to form cracks extending from an indentation, using a micro Vickers hardness meter, the length of the cracks from four corners of the indentation is 15 μm or less.

6. A method for evaluating a piezoelectric layer, the method comprising:
pressing a diamond conical indenter having an angle of 136° between opposite faces into the piezoelectric layer at a load of 5 gf for 5 seconds using a micro Vickers hardness meter, thereby forming cracks extending from an indention; and
measuring the length of the cracks from four corners of the indentation.

* * * * *